United States Patent
Chambon et al.

(10) Patent No.: US 8,877,982 B2
(45) Date of Patent: Nov. 4, 2014

(54) PROCESS FOR TRANSFORMATION OF LIGNOCELLULOSIC BIOMASS OR CELLULOSE BY TUNGSTEN-OXIDE-BASED SOLID LEWIS ACID CATALYSTS AND A METAL THAT IS SELECTED FROM GROUPS 8 TO 11

(75) Inventors: Flora Chambon, Bron (FR); Nadine Essayem, Saint Just Chaleyssin (FR); Franck Rataboul, Lyons (FR); Catherine Pinel, Lyons (FR); Amandine Cabiac, Givors (FR); Emmanuelle Guillon, Vourles (FR)

(73) Assignees: IFP Energies Nouvelles, Rueil-Malmaison Cedex (FR); Centre National de la Recherche Scientifique, Paris Cedex (FR)

( * ) Notice: Subject to any disclaimer, the term of this patent is extended or adjusted under 35 U.S.C. 154(b) by 0 days.

(21) Appl. No.: 13/812,921

(22) PCT Filed: Jul. 19, 2011

(86) PCT No.: PCT/FR2011/000424
§ 371 (c)(1),
(2), (4) Date: Apr. 4, 2013

(87) PCT Pub. No.: WO2012/022853
PCT Pub. Date: Feb. 23, 2012

(65) Prior Publication Data
US 2013/0184496 A1    Jul. 18, 2013

(30) Foreign Application Priority Data

Jul. 29, 2010 (FR) .................................... 10 03180

(51) Int. Cl.
| | | |
|---|---|---|
| C07C 45/51 | (2006.01) | |
| C07C 29/14 | (2006.01) | |
| B01J 37/02 | (2006.01) | |
| B01J 37/30 | (2006.01) | |
| C07C 29/00 | (2006.01) | |
| B01J 37/08 | (2006.01) | |
| C07C 45/60 | (2006.01) | |
| B01J 23/652 | (2006.01) | |

(52) U.S. Cl.
CPC ............. *C07C 45/51* (2013.01); *B01J 37/0209* (2013.01); *B01J 37/30* (2013.01); *C07C 29/00* (2013.01); *B01J 37/086* (2013.01); *C07C 45/60* (2013.01); *B01J 23/6527* (2013.01); *B01J 37/0201* (2013.01)
USPC .......................................... 568/386; 568/863

(58) Field of Classification Search
USPC .................................. 568/386, 863
See application file for complete search history.

(56) References Cited

U.S. PATENT DOCUMENTS 2,488,722 A    11/1949  Gurkan

FOREIGN PATENT DOCUMENTS

CN        101768050 A    7/2010

OTHER PUBLICATIONS

International Search Report for International Application No. PCT/FR2011/000424 (Nov. 15, 2011).
Database WPI XP002625856 (Jul. 7, 2010) "Production of Ethylene Glycol and 1,2-Propanediol, by Reacting Cellulose and Comprising Ruthenium Catalyst Loaded on Activated Carbon, and Tungsten Oxide".

*Primary Examiner* — Sikarl Witherspoon
(74) *Attorney, Agent, or Firm* — Millen, White, Zelano & Branigan, P.C.

(57) ABSTRACT

The invention relates to a process for transformation of ligno-celiulosic biomass or cellulose that uses tungsten-oxide-based heterogeneous catalysts that are dispersed on an oxide-based substrate, preferably with a base of oxide(s) of aluminum and/or zirconium and/or titanium and/or niobium and containing an element in the particular metallic state. The use of these catalysts makes it possible to obtain directly upgradable products containing three carbon atoms, in particular hydroxyacetone and propylene glycol with high selectivity.

20 Claims, No Drawings

PROCESS FOR TRANSFORMATION OF LIGNOCELLULOSIC BIOMASS OR CELLULOSE BY TUNGSTEN-OXIDE-BASED SOLID LEWIS ACID CATALYSTS AND A METAL THAT IS SELECTED FROM GROUPS 8 TO 11

FIELD OF THE INVENTION

The invention relates to a process for transformation of lignocellulosic biomass or cellulose directly into upgradable products that contain three carbon atoms that use heterogeneous catalysts.

PRIOR ART

For several years, there has been a very sharp resurgence of interest for the incorporation of products of renewable origin within the fuel and chemistry branches, in addition to or in place of products of fossil origin. One possible method is the conversion of cellulose, contained in the lignocellulosic biomass, into chemical products or intermediate products, such as the products that contain three carbon atoms, such as hydroxyacetone and propylene glycol.

The term lignocellulosic biomass (BLC) or lignocellulose encompasses several products that are present in variable quantities according to the origin thereof: cellulose, hemicellulose and lignin. The hemicellulose and cellulose constitute the carbohydrate portion of the lignocellulose. These are polymers of sugars (pentoses and hexoses). Lignin is a macromolecule that is rich in phenolic units. Lignoceilulosic biomass is defined as, for example, the products that are obtained from forestry operations and the sub-products that are obtained from agriculture, such as straw as well as certain dedicated plants with a high agricultural yield.

The production of chemical products from lignocellulosic biomass makes it possible both to reduce the energy dependency relative to petroleum and to protect the environment through the reduction of greenhouse gas emissions without using resources designed for food uses.

The direct transformation of lignocellulosic biomass or cellulose into chemical products or intermediate products, in particular those containing three carbon atoms such as hydroxyacetone and propylene glycol, is a particularly advantageous method. Direct transformation is defined as the transformation of a stage of lignocellulosic biomass or cellulose, optionally pretreated, into upgradable products that contain three carbon atoms, such as hydroxyacetone and propylene glycol.

Hydroxyacetone, or acetol, has $C_3H_6O_2$ as its chemical formula, and its structure is reflected in its systematic name, 1-hydroxy-propaone. Hydroxyacetone is used, for example, as a chemical intermediate product and as a monomer for the synthesis of polyols, but also as a chemical solvent.

The production of hydroxyacetone can be done by a chemical method or by a biological method, The chemical methods for the production of hydroxyacetone that are known to one skilled in the art are carried out via the transformation of petrochemical intermediate products such as the hydration of propylene. The oxidation of 1,2-propanediol produced by a biological method can also lead to the formation of hydroxyacetone.

Propylene glycol, or propane-1,2-diol, has $C_3H_8O_2$ as its chemical formula, and its structure is reflected in its systematic name, 1,2-dihydroxypropane. The applications of propylene glycol are numerous and diverse: for example, its use as food additive, emulsifying agent, intermediate product of unsaturated polyesters, but also that of cooling liquid or its use in the textile industry will be cited.

The production of propylene glycol is industrially implemented by hydration of the propylene oxide.

The upgrading of the lignoceliulosic biomass or the cellulose that is contained in the biomass by heterogeneous catalysis is described in the literature. The patent application EP-A1-B 2011 569 describes the hydrolysis of the cellulose into sorbitol or into mannitol in an aqueous medium with heterogeneous metallic, catalysts.

The patent application WO 03/035582 describes the hydrogenolysis of sorbitol at 200° C. by using (Ni, Re)/C catalysts that leads to yields of 30% of diols such as ethylene glycol and propylene glycol.

The production of propylene glycol by treatment of cellulose under hydrothermal conditions in the presence of heterogeneous Ru/C catalysts is observed by Luo et al. (Angew. [Applied] Chem. Int. Ed. 2007, 46, 7636-7639). The maximum carbon yield that is obtained of propylene glycol is 2.2% by weight for reactions conducted at a temperature of 245° C., and an $H_2$ pressure of 6 MPa, in an aqueous medium. Under these reaction conditions, the conversion of cellulose is approximately 39%. The production of hydroxyacetone is not reported.

Ji et al. (Angew, Chem. Int. Ed. 2008, 47, 8510-8513) also studied the reaction for transformation of the cellulose in a hydrothermal environment by using carbon-substrate tungsten-carbide-based catalysts with nickel as a promoter, making progress in good selectivity of ethylene glycol and sorbitol with this type of catalyst. The operating conditions are a temperature on the order of 245° C. and a hydrogen pressure of 6 MPa, in the presence of water. The maximum mass yield of 1,2-propylene glycol is 7.7% for a carbon-substrate nickel-tungsten carbide catalyst. By using a 2.5% $Pt/Al_2O_3$-type catalyst, the mass yield of propylene glycol is 9.3%. The conversion of cellulose is total in the two cases.

There again, the production of hydroxyacetone is not mentioned.

Likewise, Zhang et al. (Chem. Commun., 2010, 46, 862-864) recently made progress in directly converting cellulose into ethylene glycol by tungsten-carbide-based catalysts with substrates of carbon materials of commercial silica. During these experiments, with a temperature on the order of 245° C. and a hydrogen pressure of 6 MPa, in aqueous medium, the maximum mass yield of propylene glycol is 8.4%, the conversion of cellulose is total, and the formation of hydroxyacetone is not observed.

The same research team made progress in converting cellulose into ethylene glycol by nickel-tungsten catalysts with an SBA-15-type mesopore silica substrate (Zheng et al., ChemSusChem., 2010, 3, 63-66), Once again, a total conversion of cellulose is obtained with a low maximum mass yield of propylene glycol (on the order of 4%) and without formation of hydroxyacetone.

Finally, non-catalytic and thermal conversion processes such as pyrolysis or direct liquefaction of the lignocellulose lead to the production of biomass liquefiers. The minor presence of hydroxyacetone is sometimes noted. For example, Patwardhan et al., Bioresource Technology, 2010, 101, 4646-4655, will be cited. Nevertheless, aside from their application conditions (temperature, pressure), these non-catalytic processes are very far removed from the process that is the object of the invention.

Thus, no process that allows a direct transformation of cellulose or, more broadly, lignocellulosic, biomass, optionally pretreated, into upgradable products containing three carbon atoms, in particular hydroxyacetone and propylene glycol, in a highly selective way by means of heterogeneous catalysts of the type of those described in this invention is reported in the literature.

SUMMARY OF THE INVENTION

The applicants discovered a process for direct transformation of cellulose, present in the lignocellulosic biomass, optionally pretreated, into upgradable products containing three carbon atoms, using heterogeneous catalysts based on tungsten oxide dispersed on an oxide substrate and containing an element in the metallic state selected from groups 8 to 11 of the periodic table.

DETAILED DESCRIPTION OF THE INVENTION

The invention relates to a process for transformation of the lignocellulosic biomass or cellulose into hydroxyacetone and propylene glycol, in which the lignocellulosic biomass or cellulose is brought into contact, under hydrothermal conditions and under a reducing atmosphere, with a tungsten-oxide-based heterogeneous catalyst dispersed on an oxide-based substrate and containing at least one element in the metallic state that is selected from groups 8 to 11 of the periodic table, said catalyst having Lewis-type acid sites.

The process according to the invention makes it possible to obtain in a selective way a mixture of products comprising hydroxyacetone and propylene glycol in a significant quantity.

During the transformation of the feedstock, it is possible to obtain a mixture of different products comprising in particular glucose, sorbitol, lactic acid, formic acid, levulinic acid, acetic acid, hydroxyacetone, propylene glycol, 2,5-hexanedione, (hydroxymethylfurfural), 1,2-hexanediol, soluble products and soluble oligosaccharides and polymers.

The process makes it possible to obtain high conversions of the reagent and important selectivities, in particular high yields of hydroxyacetone and propylene glycol, while limiting the formation of oligosaccharides or water-soluble polymers. These conversions and selectivities are Obtained only under hydrothermal conditions (presence of water), while operating under reducing atmosphere, and in the presence of tungsten-oxide-based catalysts that have Lewis-type acid properties and that contain an element in the metallic state that is selected from groups 8 to 11. Actually, the solid catalysts for the most part having a Brønsted acidity promote the production of soluble oligosaccharides and/or soluble polymers, exhibiting a lower selectivity in desired chemical intermediate products. In contrast, the tungsten-oxide-based catalysts have Lewis-type acid properties and, not containing metal, do not lead to the formation of the desired chemical intermediate products but make it possible to obtain lactic acid selectively.

Thus, the molar yield of hydroxyacetone and propylene glycol is greater than the yield of each of the other products obtained during the transformation of the lignocellulosic biomass and is also greater than the sum of the yields of the different products taken as a whole.

Said oxide-based substrate is preferably selected from the group formed by the oxides of aluminum and/or zirconium and/or titanium and/or niobium.

The content of Lewis-type acid sites of the catalyst is preferably higher than 50%. The use of these catalysts makes it possible to obtain directly upgradable products that contain three carbon atoms, in particular hydroxyacetcone and propylene glycol, of high selectivity while limiting the production of soluble oligosaccharides and polymers.

The process according to this invention makes it possible also to improve the conversion of the cellulose that is present in the lignocellulosic biomass.

The Feedstock

The lignocellulosic biomass essentially consists of three natural components that are present in variable amounts according to the origin thereof: cellulose, hemicellulose, and lignin.

The cellulose $(C_6H_{10}O_5)_n$, represents the major portion (40-60%) of the composition of the lignocellulosic biomass. This is a semi-crystalline linear homopolymer of glucose. The cellulose is insoluble in water at ambient temperature and pressure.

Hemicellulose is the carbohydrate that is second in quantity after cellulose and constitutes 20 to 40% by weight of the lignocellulosic biomass. In contrast to cellulose, this polymer consists for the most part of monomers of pentoses (cyclic compounds with five atoms) and hexoses (cyclic compounds with 6 atoms). Hemicellulose is an amorphous heteropolymer with a degree of polymerization that is less than that of cellulose (30-100) and that is generally water-soluble, Lignin is an amorphous macromolecule that is present in the lignocellulosic compounds in variable proportions according to the origin of the material (straw~15%, wood: 20-26%). Its function is mechanical reinforcement, hydrophobization, and support of plants. This macromolecule that is rich in phenolic units can be described as a resultant of the combination of three monomer units of the propyl-methoxyphenol type. Its molar mass varies from 5,000 g/mol to 10,000 g/mol for hardwoods and reaches 20,000 g/mol for softwoods.

The lignocellulosic raw material can consist of wood or plant waste. Other nonlimiting examples of lignocellulosic biomass material are waste from agricultural operations (straw, grasses, stems, pits, shells, . . . ), waste from forestry operations (initial cutting products, bark, sawdust, chips, scraps, . . . ), products from forestry operations, dedicated crops (short-rotation shrubs), waste from the food-processing industry (waste from the industry of cotton, bamboo, sisal, banana, corn, switchgrass, alfalfa, coconut, bagasse, . . . ), household organic waste, waste from wood transformation plants, scrap wood from construction, and paper, which may or may not be recycled.

The feedstock that is used in the process according to the invention is lignoceilulosic biomass or cellulose. The cellulose that is used may be crystalline or amorphous.

The lignocellulosic biomass feedstock can be used in its raw form, i.e., in its entirety of these three cellulose, hemicellulose and lignin components. The raw biomass generally comes in the form of fibrous residues or powder. In general, it is ground or shredded to allow its transport.

The lignocellulosic biomass feedstock can also be used in its pretreated form, in a form that contains at least one cellulosic portion after extraction of lignin and/or hemicellulose.

The biomass preferably undergoes a pretreatment so as to increase the reactivity and the accessibility of cellulose within the biomass before its transformation. These pretreatments are of a mechanical, thermochemical, thermomechanical-chemical and/or biochemical nature and bring about the decrystallization of cellulose, the solubilization of hemicellulose and/or lignin, or the partial hydrolysis of hemicellulose following the treatment.

The lignocellulosic biomass feedstock can also be pretreated so as to be in the form of water-soluble oligomers. These pretreatments are of a mechanical, thermochemical, thermo-mechanical-chemical and/or biochemical nature.

They bring about the decrystallization and the solubilization of the cellulose in the form of water-soluble oligomers.

The mechanical treatments go beyond simple shredding because they modify the chemical structure of the components. They improve the accessibility and the reactivity of cellulose by its decrystallization and by the increase in the exchange surface area. The mechanical treatments include the reduction of the size of fibers or elementary particles, for example by chipping the biomass with a cutter, by grinding the biomass (adjustment of the grain size), destructuring chips on a press, or grinding by chip abrasion, after preheating. The mechanical treatments can be performed in decentralized mode close to where the biomass is produced or in a centralized mode that directly feeds the transformation.

The thermochemical treatments include the baking of the biomass at high temperature (150-170° C.) in a dilute acid medium (primarily sulfuric acid, but also phosphoric acid, acetic acid, or formic acid), in an alkaline medium (soda, sulfites, lime, . . . ) or in an oxidizing medium (wet oxidation with air or oxygen; peroxide in an alkaline medium; peracetic acid). The other thermoehemical treatments include treatments with solvents (hot ethanol) or roasting that can be defined as pyrolysis at moderate temperature and with a controlled dwell time because it is accompanied by partial destruction of the lignocellulosic material. The known technologies for roasting are, for example, the rotary kiln, moving bed, fluidized bed, heated endless screw, and the contact with metal balls that provide heat, These technologies can optionally use a gas that circulates in co-current or counter-current such as nitrogen or any other inert gas under the conditions of the reaction, The thereto-mechanical-chemical treatments include vapor treatments (vapor explosion also called flash hydrolysis or "steam explosion"), the APEX (ammonia fiber explosion) treatment with ammonia, or two-screw extrusion with various chemical reagents.

The pretreatment makes it possible to prepare the lignocellulosic biomass by separating the carbohydrate portion of the lignin and by adjusting the size of the biomass particles that are to be treated. The size of the biomass particles after pretreatment is generally less than 5 mm, preferably less than 500 microns.

The Catalyst

The catalysts that are used for the transformation of the lignocellulosic biomass or cellulose according to this invention are based on tungsten oxide that is dispersed on the surface of an oxide substrate and contain an element in the metallic state that is selected from groups 8 to 11 of the periodic table.

In a general manner, the acidity of a catalyst is the resultant of two combined types of acidity: Lewis acidity, characterized by the presence of an electron gap on an atom, and Brønsted acidity, characterized by a capability of giving up a proton. The nature of the acid sites can be characterized by adsorption of pyridine followed by IR spectroscopy in accordance with the method that is described in [M. Guisnet, P. Ayrault, C. Coutanceau, M. F. Alvarez, J Datka, *J. Chem, Soc., Faraday Trans.* 93, 1661 (1997)].

The solids that are used in the process according to the invention are characterized by superficial acidic properties that are for the most part of the Lewis acid type.

In a preferred way, the catalyst has a content of Lewis acid sites that is greater than 50%. The Lewis-type acid sites are associated with the presence of tungsten radicals coordinatively unsaturated but also with radicals that are characteristic of the substrate: $Al^{3+}$, $Zr^{4+}$, $Ti^{4+}$, and $Nb^{5+}$. It is known that the coordination of the surface tungsten radicals (tetrahedral/octahedral) depends on their dispersion, the tungsten content, the nature of the precursors, and the heat treatments.

The zirconitun-tungstate-type catalysts, ZrW, combined or not with a metallic phase, are described for being active in many applications such as the hydroisomerization of paraffins (U.S. Pat. No. 6,124,232) or the dimerization of olefins (U.S. Pat. No. 5,453,556), Zirconium tungstate is commonly prepared by impregnation or co-precipitation: the tungsten oxides with substrates of zirconia were described for the first time by Hino and Anita. (J. Chem. Soc., Chem, Commun., 1148 (1979)). This solid is obtained by impregnation of zirconia by ammonium metatungstate, followed by decomposition in air at 800-850° C. The U.S. Pat. No. 5,510,309 discloses a solid that is obtained by co-precipitation of ammonium metatungstate and $ZrOCl_2$, followed by calcination at a temperature of higher than 700° C.

The catalysts that are used in the invention contain, in addition to the tungsten oxide dispersed on the surface of the substrate, a particular metal, in the metallic state, selected from groups 8 to 11 of the periodic table, The tungsten-oxide-based catalysts dispersed on the surface of an oxide substrate used in the process according to this invention can be synthesized by ion exchange or by impregnation followed by a heat treatment.

The solids that are obtained have the advantages of being mesoporous and stable, thermally and under hydrothermal conditions.

The tungsten content is between 2 to 30% by weight, preferably between 10 and 20%, with the percentages being expressed in terms of % by weight of metal relative to the total mass of catalyst.

The tungsten precursors are selected from among tungstic acid, peroxotungstic acid, ammonium metatungstate, or tungsten-based isopolyanions or heteropolyanions. The ammonium metatungstate is the usual precursor. The use of tungstic acid in solution in hydrogen peroxide is preferred because by this method, the formation of monomeric tungsten radicals in solution—radicals that are exchangeable at acidic pH with substrates based on Zr, Ti, Al and/or Nb according to the patent application WO 2004/004893—is promoted.

A preparation method consists of an anion exchange between a tungstic acid solution in hydrogen peroxide and the hydroxide of zirconium and/or titanium and/or aluminum and/or niobium, followed by a calcination according to U.S. 2006/0091045.

The presence of tungsten on the oxide-based substrate brings about the formation of tungsten oxide.

The element in the metallic state present in the catalyst used according to this invention is a metal that is selected from a metal of groups 8 to 11 of the periodic table. It is selected from among Fe, Co, Ni, Ru, Rh, Pd, Os, Ir, Pt or Cu, Au, Ag. In a preferred manner, the element is selected from among Pt, Ni, Ru, Cu. In a very preferred manner, it involves platinum.

The metal precursors can be, without limiting the origin thereof, metallic organic complexes, metal salts. For the metal salts, for example, the metal chlorides and metal nitrates will be cited, The introduction of metal can be done by any technique that is known to one skilled in the art, such as, for example, ion exchange, dry impregnation, excess impregnation, vapor phase deposition, etc. The introduction of metal can be done before or after the shaping of the tungsten-oxide-based catalyst that is dispersed on an oxide-based substrate.

The content by weight of the metal element that is introduced is advantageously between 0.01 and 10% by weight, and preferably between 0.05 and 5% by weight relative to the total mass of the catalyst.

The stage for introduction of the metal element is followed by a heat treatment stage. The heat treatment is advantageously carried out between 300° C. and 700° C. The heat treatment stage can be followed by a temperature reduction treatment. The reducing heat treatment is advantageously carried out at a temperature of between 200° C. and 600° C. under a stream of hydrogen or under hydrogen atmosphere.

The reduction stage can be carried out in-situ, i.e., in the reactor where the reaction takes place, before the introduction of the reaction feedstock. The reduction can also be carried out ex-situ.

In a preferred manner, the size of the metal particles of the catalyst used in the process according to the invention is less than 10 nm.

The catalysts that are used in this invention can be in the form of powder, extrudates, balls or pellets. The shaping can be done before or after the metal is introduced.

The catalysts that are used in this invention are characterized by the techniques that are known to one skilled in the art. Transmission microscopy will be cited, for example, for characterizing the metallic phase.

Transformation Process

The process for transformation of the lignocellulosic biomass or cellulose according to the invention comprises the reaction in a water-containing medium in the presence of the catalytic composition according to the invention.

Water-containing medium refers to the conventional liquid media (such as, for example, ethanol or water) and the non-conventional media, such as the ionic liquids or the supercritical media of liquid-type density.

The content by mass of water in the medium is generally greater than 1%. Preferably, the medium is water.

The process for transformation of the lignocellulosic biomass or the cellulose according to the invention is carried out under reducing atmosphere, preferably under hydrogen atmosphere. The hydrogen can be used in pure form or in a mixture.

The process is carried out at temperatures of between 160° C. and 250° C., preferably between 175° C. and 230° C., and at a pressure of between 0.5 MPa and 20 MPa, preferably between 2 MPa and 10 MPa.

In general, the reaction can be performed according to different embodiments. Thus, the reaction can be implemented intermittently or continuously, for example in a fixed bed, It is possible to operate with a closed or half-open reactor, The catalyst is introduced into the reactor at a rate of a quantity that corresponds to a biomass/catalyst mass ratio of between 1 and 1,000, preferably between 1 and 500, preferably between 1 and 100, preferably between 1 and 50, and even preferably between 1 and 25.

The catalyst that is introduced into the reactor can undergo a reducing heat treatment stage before the introduction of the reaction feedstock. The reducing heat treatment is carried out at a temperature of between 200° C. and 600° C. under a stream of hydrogen or under hydrogen atmosphere.

The biomass is introduced into the process at a rate of a quantity that corresponds to a (water-containing medium)/biomass mass ratio of between 1 and 1,000, preferably between 1 and 500, and even preferably between 5 and 100. The dilution rate of the biomass is therefore between 1:1 and 1:1,000, preferably between 1:1 and 1:500, and even preferably between 1:5 and 1:100.

If a continuous process is selected, the mass speed per hour (mass/catalyst mass feedstock flow rate) is between 0.01 and 5 $h^{-1}$, preferably between 0.02 and 2 $h^{-1}$.

The Products that are Obtained and their Mode of Analysis

After the reaction, the reaction medium is sampled and centrifuged. The reaction liquid is next analyzed by high-pressure liquid chromatography (HPLC) by using refractometry for determining the content of conversion products of the aqueous solution.

The products of the reaction are soluble in water. They consist of monosaccharides and their derivatives, oligosaccharides, but also soluble polymers that are formed by successive combinations of the derivatives of monosaccharides.

Monosaccharides refer to the simple sugars (hexoses, pentoses) that are produced by complete depolymerization of cellulose and/or hemicellulose, in particular glucose, mannose, xylose, fructose, . . . .

Monosaccharide derivatives refer to the products that can be obtained by dehydration, isomerization, reduction or oxidation:

Alcohol sugars, alcohols and polyols: in particular sorbitol, xylitol, glycerol, ethylene glycol, propylene glycol, ethanol, hydroxyaeetone . . . , Ketones, hexane-diones: 2,5-hexanedione, hydroxyacetone . . . , Carboxylic acids and their esters, lactones: formic acid, levulinic acid, alkyl levulinates, lactic acid, alkyl lactates, glutaric acid, alkyl glutarates, 3-hydroxypropanoic acid, 3-hydroxybutyrolactone, γ-butyrolactone, Cyclic ethers: for example, tetrahydrofuran (Tiff), methyltetrahydrofuran (Me-THF), dicarboxylic acid furan, 5-(hydroxymethyl)furfural . . . .

Oligosaccharides refer to a carbohydrate that has as its composition $(C_6H_{10}O_5)_n$, where n is greater than 1, obtained by partial hydrolysis of cellulose, or hemicellulose, or starch.

Soluble polymers refer to all of the products that are obtained from condensation between monosaccharides, oligosaccharides and/or derivatives of monosaccharides.

The quantity of water-soluble reaction products (monosaccharides and derivatives, oligosaccharides, soluble polymers) is determined by the COT [TOC] (Total Organic Carbon) analysis that consists of the measurement of carbon in solution. The quantity of monosaccharides and their derivatives is determined by HPLC analyses.

The conversion is defined as the percentage of solubilization of the biomass or cellulose and is calculated according to the following equation:

$$C = 100 * C_{solubilized} / C_{initial}$$

in which $C_{solubilized}$ represents the quantity of solubilized carbon that is analyzed by TOC (mg), and $C_{initial}$ represents the quantity of carbon at the beginning of the reaction that is contained in the biomass or solid cellulose.

The molar yields of glucose derivatives are calculated by means of HPLC analysis. Each compound is corrected by the carbon atom number contained in the glucose unit.

The molar yields of a derivative i are calculated as follows:

$$Rdti = 1.00 * (nC_{Pi}/6) * (P_i/Glu_0)$$

where $nC_{Pi}$ represents the number of carbon atoms of the derivative i, Pi represents the number of moles of the product $P_i$, and $Glu_0$ represents the number of moles of glucose units contained in the biomass or cellulose at the beginning of the reaction.

The formations of oligosaccharides and soluble polymers correspond to a loss of carbon. This loss of carbon is deduced from TOC and HPLC analyses. The yield of oligosaccharides and soluble polymers is calculated according to the following equation:

$$Rdt_{olig} = C - \Sigma rdt_i$$

where C represents the conversion of the cellulose and $\Sigma rdt_i$ represents the sum of molar yields of all of the monosaccharides and their derivatives that are analyzed by HPLC.

EXAMPLES

Example 1

Preparation of Catalyst C1 (According to the Invention): Platinum on a Zirconium Tungstate Substrate Zirconium tungstate was synthesized in accordance with the teaching of the patent application U.S. 2006/0091045. Zirconium hydroxide, obtained from a zirconyl chloride solution and an ammonia solution, is dried and then subjected to an ion exchange for 15 minutes by using a 0.25 M tungstic acid solution in 30% hydrogen peroxide (150 ml). The solid that is obtained is filtered and then dried at 80° C. for 24 hours. Next, the solid that is obtained is calcined under a flow of dry air at the temperature of 700° C. for 3 hours.

The zirconium tungstate that is obtained contains 11.7% by weight of tungsten, The nature of the acid sites of this catalyst is characterized by pyridine adsorption followed by IR spectroscopy: more than 65% of the acid sites of this tungsten-based catalytic formulation are Lewis-type acid sites.

An aqueous solution of hexachloroplatinic acid $H_2PtCl_6 \cdot xH_2O$ with 8% by weight (1 ml, 0.525 g) is added at ambient temperature to zirconium tungstate (1 g) that is previously desorbed under vacuum (1 h, 100° C.). The mixture is stirred for one hour and then is evaporated. The solid that is obtained is next put out to dry in the oven at 110° C. for 24 hours. Next, the catalyst is calcined under a stream of dry nitrogen at the temperature of 550° C. for two hours and then reduced under a stream of hydrogen to 300° C. for two hours. The catalyst C1 that is obtained contains 2.1% by weight of platinum with a mean diameter of platinum particles of 2.9 nm.

Example 2

Preparation of Catalyst C2 (According to the Invention): Platinum on an Aluminum Tungstate Substrate An aluminum tungstate is prepared by using aluminum hydroxide (boehmite) and tungstic acid as raw material. 10 g of aluminum hydroxide is subjected to an anion exchange with tungstic acid in solution (0.25 M) in 150 ml of 30% hydrogen peroxide. The exchange lasts for 15 minutes at ambient temperature. The solid that is obtained is next filtered and then dried at 80° C. for 24 hours.

Next, the solid is calcined under a flow of dry air at the temperature of 700° C. for 3 hours. At the end of these treatments, the aluminum tungstate that is obtained contains 18% by weight of tungsten.

An aqueous solution of hexachloroplatinic acid $H_2PtCl_6 \cdot xH_2O$ at 8% by weight (1.3 ml, 0.525 g) is added at ambient temperature to the aluminum tungstate (1 g) that was previously desorbed under vacuum (1 h, 1.00° C.). The mixture is stirred for one hour and then is next evaporated. The solid that is obtained is next put out to dry in the oven at 110° C. for 24 hours. Next, the catalyst is calcined under a flow of dry nitrogen at the temperature of 550° C. for two hours and then reduced under a stream of hydrogen at 300° C. for two hours.

The catalyst C2 that is obtained contains 1.9% by weight of platinum with a mean diameter of platinum particles of 1.1 nm.

Example 3

Preparation of a Catalyst C3 Not According to the Invention): Platinum on a Silica Substrate The raw material that is used is the Alfa Aesar commercial substrate $SiO_2$ with a specific surface area of 300 $m^2/g$. Typically, an aqueous solution of tetramine platinum (1.3 mu 1 0.171 g) is added at ambient temperature to silica (1 g) that was previously desorbed under vacuum (1 hour, 100° C.). The mixture is stirred for one hour, and then is next evaporated. The solid that is obtained is next put out to dry in the oven at 110° C. for 24 hours. Next, the catalyst, is calcined under a flow of dry nitrogen at the temperature of 500° C. for two hours and then reduced under a stream of hydrogen to 300° C. for two hours.

The catalyst C3 that is obtained contains 1.6% by weight of platinum with a mean diameter of platinum particles of 4.6 nm.

Example 4

Transformation of Celluse that Uses Catalysts that are Prepared in Examples 1 to 3

This example relates to the conversion of cellulose from catalysts C1, C2 and C3 for the production of upgradable products C3, and in particular hydroxyacetone and propylene glycol.

65 ml of water, 1.6 g of Avicel® cellulose (70% crystallinity) and 0.68 g of catalyst C1, C2 or C3 are introduced into a 100 ml autoclave. The autoclave is heated to 190° C., and a pressure of 5 MPa of hydrogen is introduced. After 24 hours of reaction, the reaction medium is sampled and centrifuged. The reaction liquid is next analyzed by high-pressure liquid chromatography (IIPLC) by using refractometry for determining the content of conversion products of the aqueous solution.

The conversion of cellulose is also carried out in the absence of catalyst by way of comparison, In addition, the metal-free tungstate oxide substrates, or the solids AlW and ZrW, are evaluated.

The results that are obtained are referenced in Table 1.

TABLE 1

Conversion of Cellulose, Yields of Lactic Acid, Hydroxyacetone, Propylene Glycol, and Total Yield of $C_3$ Products.

| | Molar Yield (%) | | | | | |
|---|---|---|---|---|---|---|
| Catalyst | Cellulose Conversion (%) | Lactic Acid (%) | Hydroxy-acetone (HA) (%) | Propylene Glycol (PG) (%) | Sum of the HA and PG Products | Sum of the Other Products |
| Without Catalyst | 32 | 4 | 2 | 0 | 2 | 30 |
| PtZrW (C1, Example 1) | 59 | 3 | 28 | 8 | 36 | 30 |

TABLE 1-continued

Conversion of Cellulose, Yields of Lactic Acid, Hydroxyacetone, Propylene Glycol, and Total Yield of $C_3$ Products.

| | Molar Yield (%) | | | | | |
|---|---|---|---|---|---|---|
| Catalyst | Cellulose Conversion (%) | Lactic Acid (%) | Hydroxy-acetone (HA) (%) | Propylene Glycol (PG) (%) | Sum of the HA and PG Products | Sum of the Other Products |
| ZrW | 65 | 14 | 7 | 0 | 7 | 58 |
| Pt/AlW (C2, Example 2) | 70 | 1 | 28 | 20 | 48 | 22 |
| AlW | 55 | 28 | 3 | 0 | 3 | 52 |
| Pt/SiO$_2$ (C3, Example 3, Anomalous) | 28 | 1 | 7 | 1 | 8 | 20 |

For the catalyst Pt/SiO$_2$, not in accordance with the invention, the quantity of hydroxyacetone that is formed represents 7 mol % of the quantity of initial cellulose. The quantity of hydroxyacetone and polypropylene glycol that is produced is 8 mol %. The cellulose conversion is 28%.

For the catalyst Pt/AlW, the quantity of hydroxyacetone that is formed represents 28 mol % of the quantity of initial cellulose, with 48 mol % of hydroxyacetone and propylene glycol molecules (70% selectivity). The conversion is 70%. The propylene glycol yield is 20%.

For the catalyst Pt/ZrW, the quantity of hydroxyacetone that is formed represents 28 mol % of the quantity of initial cellulose, with 36 mol % of molecules of hydroxyacetone and propylene glycol molecules (65% selectivity). The conversion is 59%.

The combination of a metallic phase Pt and a substrate with a Lewis acidity brought by tungsten proves effective in comparison with the combination of platinum and a substrate without Lewis acidity (catalysts C1 and C2 vs. catalyst C3). A molar yield of hydroxyacetone that is four times higher in the presence of tungsten and platinum is observed. The propylene glycol yield is also higher. The conversion of cellulose is improved.

In addition, the combination of platinum and a tungstate substrate shows itself to be effective in comparison with a tungstate catalyst without a metallic phase. An increase in the total conversion of 15% and in the selectivity of oxidized $C_3$ molecules of 13% in the case of the aluminum tungstate in the presence or not of platinum is observed. A difference in selectivity is observed during the addition of platinum. In the absence of platinum, high selectivity is obtained in lactic acid. In the presence of platinum, high selectivity of hydroxyacetone and propylene glycol is obtained.

Thus, these examples demonstrate the production of oxidized $C_3$ molecules with high yield and selectivity by direct transformation of cellulose via tungsten- and platinum-based heterogeneous catalysts.

The invention claimed is:

1. A process for transformation of lignocellulosic biomass or cellulose into hydroxyacetone and propylene glycol, comprising contacting the lignocellulosic biomass or cellulose, under hydrothermal conditions and under a reducing atmosphere, with a heterogeneous catalyst consisting of tungsten-oxide that is dispersed on an oxide-based substrate formed by the oxides of aluminum and/or zirconium and/or titanium and/or niobium, and containing at least one element in the metallic state from groups 8 to 11 of the periodic table, with said catalyst having Lewis-type acid sites.

2. The process according to claim 1, in which the element in the metallic state is Pt, Ni, Ru, or Cu.

3. The process according to claim 1, in which the content by weight of the element in the metallic state is between 0.01 and 10% by weight relative to the total mass of the catalyst.

4. The process according to claim 1, in which the catalyst has a content of Lewis acid sites of greater than 50%.

5. The process according to claim 1, in which the catalyst is synthesized by ion exchange or by impregnation, followed by a heat treatment.

6. The process according to claim 1, in which the transformation is implemented in a water-containing medium, with said medium being a liquid medium, an ionic liquid or a supercritical medium of liquid-type density.

7. The process according to claim 6, wherein the liquid medium is ethanol or water.

8. The process according to claim 7, wherein the content by mass of water is greater than 1%.

9. The process according to claim 7, in which the reducing atmosphere is a hydrogen atmosphere.

10. The process according to claim 9, in which the hydrogen is used in pure form or in a mixture.

11. The process according to claim 1, in which the transformation is carried out at a temperature of between 160 and 250° C., and at a pressure of between 0.5 and 20 MPa.

12. The process according to claim 1, in which the catalyst is introduced with a biomass/catalyst mass ratio of between 1 and 1,000.

13. The process according to claim 1, in which the catalyst undergoes a reducing heat treatment stage at a temperature of between 200 and 600° C. under a stream or atmosphere of hydrogen prior to the introduction of the lignocellulosic biomass into the reactor.

14. The process according to claim 1, in which the lignocellulosic biomass or cellulose is introduced with a (water-containing medium)/biomass mass ratio of between 1 and 1,000.

15. The process according to claim 1, implemented intermittently or continuously.

16. The process according to claim 15, wherein it is implemented continuously with a mass speed per hour of between 0.01 and 5 h$^{-1}$.

17. The process according to claim 1, in which the transformation is carried out at a temperature of between 175 and 230° C., and at a pressure of between 2 to 10 MPa.

18. The process according to claim 1, in which the catalyst is introduced with a biomass/catalyst mass ratio of between 1 to 500.

19. The process according to claim 1, in which the lignocellulosic biomass or cellulose is introduced with a (water-containing medium)/biomass mass ratio of between 1 to 500.

20. The process according to claim 15, implemented continuously with a mass speed per hour of between 0.02 to 2 h$^{-1}$.

* * * * *